United States Patent [19]
Yamazaki et al.

[11] Patent Number: 5,638,825
[45] Date of Patent: Jun. 17, 1997

[54] EVOKED POTENTIAL MEASURING APPARATUS

[75] Inventors: Toshimasa Yamazaki; Akihisa Kenmochi; Shinichi Fukuzumi, all of Tokyo, Japan

[73] Assignee: NEC Corporation, Tokyo, Japan

[21] Appl. No.: 426,724

[22] Filed: Apr. 21, 1995

[30] Foreign Application Priority Data

Apr. 21, 1994 [JP] Japan .................................. 6-083271

[51] Int. Cl.$^6$ ............................................. A61B 5/04
[52] U.S. Cl. ........................................ 128/731; 128/732
[58] Field of Search ................................. 128/731–739, 128/741, 745, 746; 364/413.02, 413.04

[56] References Cited

U.S. PATENT DOCUMENTS

| | | | |
|---|---|---|---|
| 5,230,344 | 7/1993 | Özdamar et al. | 128/731 |
| 5,299,118 | 3/1994 | Martens et al. | 128/731 |

FOREIGN PATENT DOCUMENTS

| | | |
|---|---|---|
| 2-1233 | 1/1990 | Japan . |
| 2-198534 | 8/1990 | Japan . |

OTHER PUBLICATIONS

Yamazaki et al., "Quantitative Evaluation of Visual Fatigue Encountered in Viewing Stereoscopic 3D Displays", Proceedings of the Society for Information Display, vol. 31, No. 3, pp. 245–247, 1990.
Nakamura et al., "Spectral sensitivity characteristics of visually evoked potentials (VEP)", Technical Report of the Television Society of Japan, vol. 10, No. 48, pp. 1–6, 1987.
Kenmochi et al., "A Virtual Reality System Using Psychological And Physiological Data", Proceedings of the 7th Symposium on Biological and Physiological Engineering, pp. 277–280, 1992.
Schimmel, "The (±) Reference: Accuracy of Estimated Mean Components in Average Response Studies", Science, vol. 157, pp. 92–94, 1967.

Primary Examiner—Lee S. Cohen
Assistant Examiner—Bryan K. Yarnell
Attorney, Agent, or Firm—Foley & Lardner

[57] ABSTRACT

An evoked potential measuring apparatus by which an evoked potential which reflects a variation in internal condition of a human being such as a feeling of strain, a feeling of irritation or a feeling of stress can be measured in a high quality with a high degree of reliability. The apparatus comprises a sensory stimulus application section, an evoked potential measurement section for measuring and amplifying an evoked brain potential, an evoked potential recording control section for controlling recording of a brain potential signal, an evoked potential recording section for recording the brain potential signal, an internal condition estimating physiological measure measurement section for measuring a physiological measure, a physiological measure signal recording control section for controlling recording of a physiological measure signal, a physiological measure signal recording section for recording the physiological measure signal, an internal condition estimation section for estimating the internal condition of the subject using the physiological measure signal, an evoked potential adding and averaging section for adding and averaging the brain potential signal in accordance with the internal condition of the subject to obtain an evoked potential, an evoked potential adoption determination section for estimating a quality of the evoked potential to determine whether or not the evoked potential may be adopted, and an evoked potential measurement procedure control section.

7 Claims, 5 Drawing Sheets

EVOKED POTENTIAL MEASURING APPARATUS

BACKGROUND OF THE INVENTION

1. Field of the Invention

This invention relates to an evoked potential measuring apparatus, and more particularly to an evoked potential measuring apparatus by which an evoked potential which reflects a variation in internal condition of a human being can be extracted in a high quality and high reliability.

2. Description of the Related Art

When some stimulation is applied to a sense of a human being, a corresponding brain potential is evoked at an information processing location of the brain which takes charge of the sense. The evoked brain potential is called evoked potential and is measured by way of electrodes from the head skin on the information processing location of the brain corresponding to the sense. An evoked potential from a stimulus to a sense is used frequently in fundamental experiments of physiology, psychology and biotechnology.

An exemplary one of methods for detecting an evoked potential is disclosed in T. Yamazaki, K. Kamijo and S. Fukuzumi, "QUANTITATIVE EVALUATION OF VISUAL FATIGUE ENCOUNTERED IN VIEWING STEREOSCOPIC 3D DISPLAYS: NEAR-POINT DISTANCE AND VISUAL EVOKED POTENTIAL STUDY", *Proceedings of the Society for Information Display*, Vol. 31, No. 3, 1990, pp.245–247. According to the method, a visually evoked potential, which is used effectively to solve the problem of fatigue, is measured for a certain period of time after a point of time at which a light is emitted as a stimulus using a flash apparatus as a light emitting element. The potential evoked at the head skin on the information processing location of the brain corresponding to the visual sensation by the stimulus of emission of light ranges ten and several microvolts to several tens microvolts. The potential is lower than a potential arising from activities from any locations of the brain than the information processing location corresponding to the visual sensation, and the potential obtained by measurement by a single stimulus may be a potential influenced by another other location of the brain than the information processing location corresponding to the visual sensation. Therefore, a similar measurement is repeated by a plurality of times, and potentials at an equal time after emission of light are added for the individual times and an average value of the potentials is calculated. The adding and averaging processing is based on the ground that, if an influence upon each measured potential of an potential from the other portions of the brain is regarded as random noise, then if the measured potentials are cumulatively added, then the noise can be reduced to zero.

Figure 6:
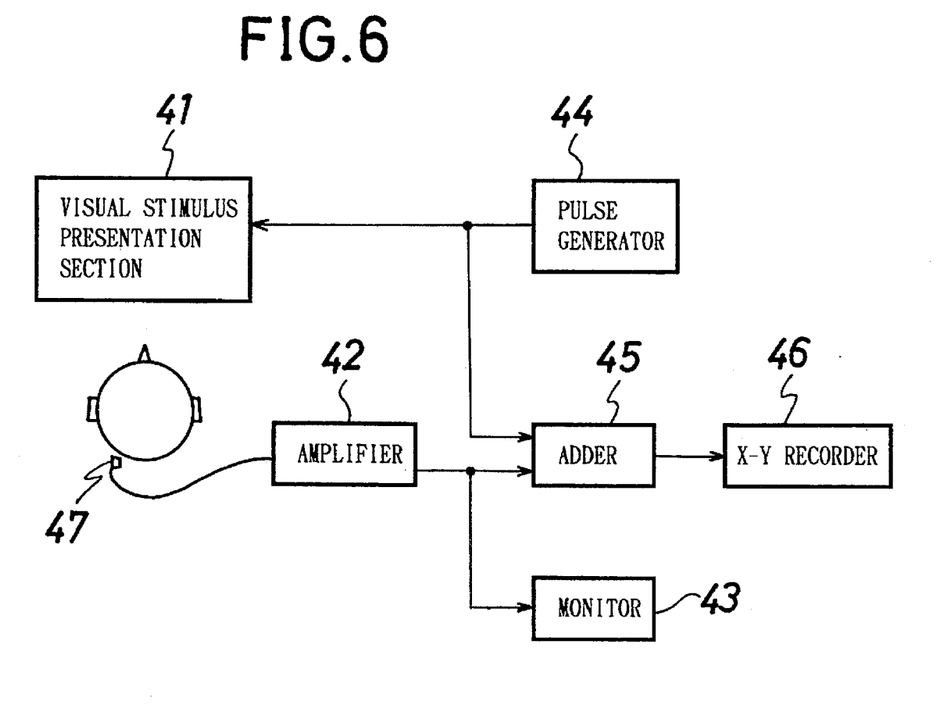
FIG. 6 is a block diagram showing a basic construction of a conventional evoked potential measuring apparatus.

An exemplary one of conventional evoked potential measuring apparatus is disclosed, for example, in T. Nakamura and Y. Morita, "Spectral sensitivity characteristics of visually evoked potentials (VEP)", *Technical Report of the Television Society of Japan*, Vol. 10, No. 48, 1987, pp.1–6. The evoked potential measuring apparatus has such a basic construction as shown in FIG. 6. Referring to FIG. 6, a visual stimulus is presented from a visual stimulus presentation section 41 in synchronism with a signal outputted from a pulse generator 44. A potential evoked when the presentation is visually sensed is inputted to an amplifier 42 by way of an electrode 47. The waveform of the signal amplified by the amplifier 42 is displayed on a monitor 43 so that an experimenter may visually observe it. Further, the amplified signal is added in an analog fashion to such signals in the past by an adder 45 in synchronism with the signal outputted from the pulse generator 44. A result of the addition is recorded as a graph onto a record paper sheet by an X-Y recorder 46.

The present day society is called a society of stress, and patients of diseases caused by stress arising from fatigue or complicated human relations are progressively increasing, for example, in places of work. Since the cause of stress lies in one's own mind, the stress originates in the function of the brain. Accordingly, also the evoked potential is considered to be/as an effective means. The visually evoked potential is effective to detect VDT (Visual Display Terminal) fatigue. However, a visually evoked potential detected by any conventional technique merely reflects the function of the visual sensation, but does not directly reflect a variation of a higher order central nervous system hidden behind a drop of the function of the visual sensation. In other words, an evoked potential detected by any conventional technique which makes use of a visual stimulus is not a brain potential which reflects a feeling of fatigue, a feeling of stress, an irritated feeling or a feeling of strain itself.

Further, even if a stimulus which induces stress is found out, any conventional technique which involves adding and averaging processing is disadvantageous in that a brain potential which reflects the function of a sense may possibly be included in a measured brain potential and it is difficult to extract only a brain potential which reflects a higher order center function.

In summary, with the conventional evoked potential measuring apparatus described above, while it is possible to detect a brain potential which reflects various functions of senses, it is impossible to measure a brain potential which relates a function of a higher order central nervous system for a feeling of strain, a feeling of irritation, a feeling of stress and so forth.

SUMMARY OF THE INVENTION

It is an object of the present invention to provide an evoked potential measuring apparatus which can measure an evoked potential which reflects a variation in internal condition of a human being such as a feeling of strain, a feeling of irritation or a feeling of stress making use of a stimulus to a sense similarly as in the conventional evoked potential measuring apparatus.

In order to attain the object described above, according to the present invention, there is provided an evoked potential measuring apparatus, which comprises sensory stimulus application means for applying a sensory stimulus to a subject, evoked potential measurement means for measuring and amplifying a brain potential evoked in response to the sensory stimulus applied to the subject, evoked potential recording control means for controlling recording of a brain potential signal outputted from the evoked potential measurement means, evoked potential recording means for recording a brain potential signal outputted from the evoked potential recording control means, internal condition estimating physiological measure measurement means for measuring a physiological measure to be used for estimation of an internal condition of the subject, physiological measure signal recording control means for controlling recording of a physiological measure signal outputted from the Internal condition estimating physiological measure measurement means, physiological measure signal recording means for recording a physiological measure signal outputted from the physiological measure signal recording control means, internal condition estimation means for estimating the internal condition of the subject using a physiological measure signal outputted from the physiological measure signal recording means, evoked potential adding and averaging means for adding and averaging a brain potential signal outputted from the evoked potential measurement means in accordance with the internal condition of the subject based on a result of estimation of the internal condition of the internal condition estimation means, evoked potential adoption determination means for estimating a quality of an evoked potential outputted from the evoked potential adding and averaging means to determine whether or not the evoked potential may be adopted, and evoked potential measurement procedure control means for controlling the sensory stimulus application means, the evoked potential recording control means, the physiological measure signal recording control means and the evoked potential adding and averaging means in accordance with a procedure for measurement of an evoked potential and a physiological measure for estimation of an internal condition.

In the evoked potential measuring apparatus, the evoked potential adding and averaging means receives the brain potential signal outputted from the evoked potential recording means and the internal condition estimated value outputted from the internal condition estimation means, and adds and averages the brain potential signal in accordance with the internal condition of the subject. Due to the function of the evoked potential adding and averaging means, it is possible to measure an evoked potential which reflects the internal condition of the subject.

Therefore, where the evoked potential measuring apparatus is used, an evoked potential which reflects an internal condition of a human being such as a feeling of fatigue, a feeling of stress, a feeling of irritation or a feeling of strain can be measured. Further, since the quality of the evoked potential thus obtained can be automatically determined, an evoked potential of a high quality can be obtained with a high degree of reliability and besides the time required for measurement of an evoked potential can be reduced remarkably.

The above and other objects, features and advantages of the present invention will become apparent from the following description and the appended claims, taken in conjunction with the accompanying drawings in which like parts or elements are denoted by like reference characters.

DESCRIPTION OF THE PREFERRED EMBODIMENT

Figure 1:
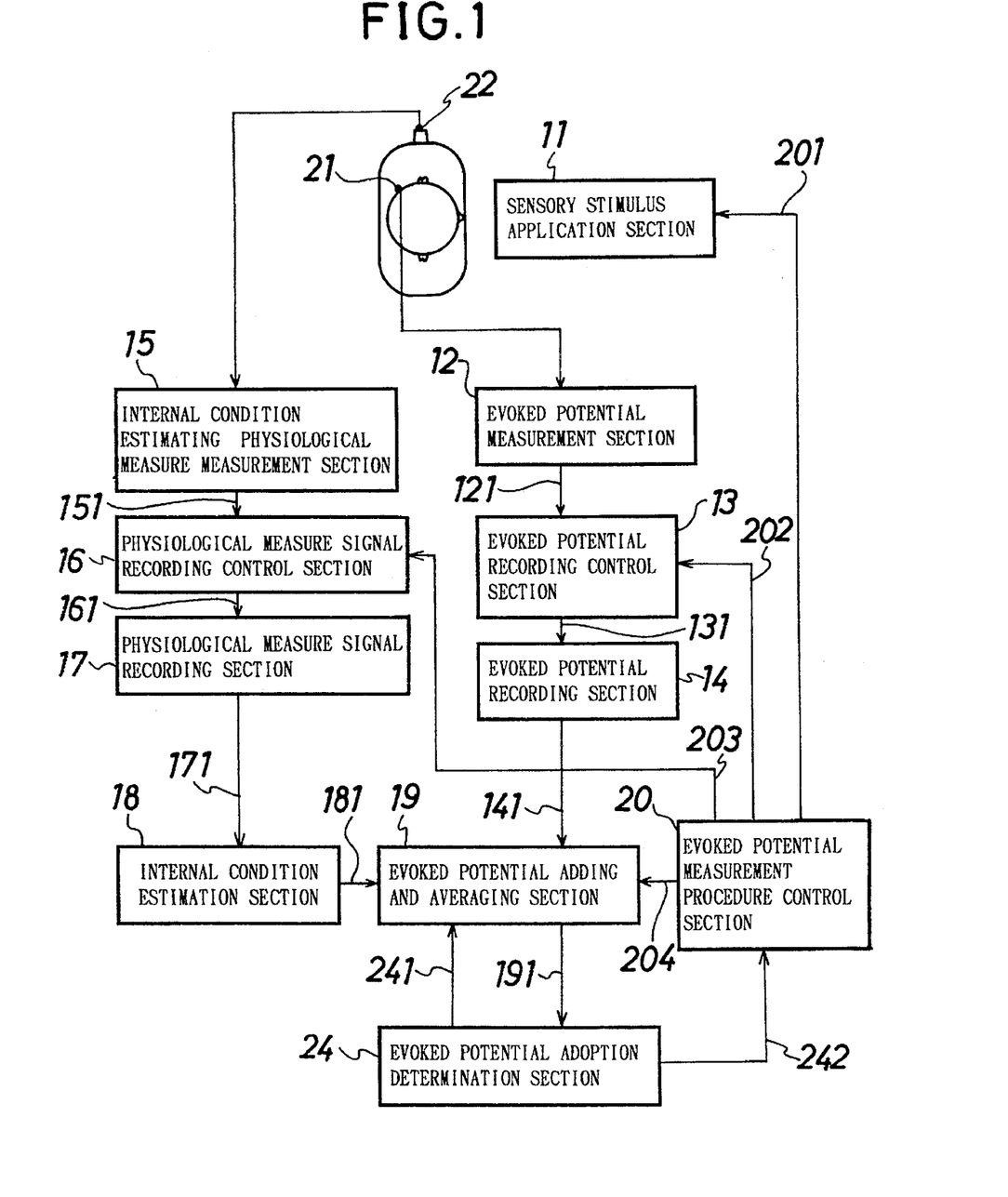
FIG. 1 is a block diagram of a basic construction of an evoked potential measuring apparatus showing a preferred embodiment of the present invention.

Referring first to FIG. 1, there is shown an evoked potential measuring apparatus according to a preferred embodiment of the present invention. The evoked potential measuring apparatus shown includes a sensory stimulus application section 11 for applying a sensory stimulus to a subject, an evoked potential measurement section 12 for measuring and amplifying a brain potential of the subject evoked by the sensory stimulus applied by the sensory stimulus application section 11, an evoked potential recording control section 13 for controlling recording of a brain potential signal outputted from the evoked potential measurement section 12, an evoked potential recording section 14 for recording a brain potential signal outputted from the evoked potential recording control section 13, an internal condition estimating physiological measure measurement section 15 for measuring a physiological measure to be utilized for estimation of an internal condition of the subject, a physiological measure signal recording control section 16 for controlling storage of a physiological measure signal outputted from the internal condition estimating physiological measure measurement section 15, a physiological measure signal recording section 17 for recording a physiological measure signal outputted from the physiological measure signal recording control section 16, an internal condition estimation section 18 for estimating the internal condition of the subject utilizing a physiological measure signal outputted from the physiological measure signal recording section 17, an evoked potential adding and averaging section 19 for adding and averaging a brain potential signal outputted from the evoked potential recording section 14 in accordance with the internal condition of the subject using a result of estimation of the internal condition of the internal condition estimation section 18 to obtain an evoked potential, an evoked potential adoption determination section 24 for estimating the quality of the evoked potential outputted from the evoked potential adding and averaging section 19 to determine whether or not the evoked potential may be adopted as an evoked potential, and an evoked potential measurement procedure control section 20 for controlling the sensory stimulus application section 11, the evoked potential recording control section 13, the physiological measure signal recording control section 16 and the evoked potential adding and averaging section 19 in accordance with a procedure for measurement of an evoked potential and a physiological measure for estimation of an internal condition.

The sensory stimulus application section 11 applies a sensory stimulus to a subject (a person whose evoked potential should be measured) in response to a signal 201 regarding a sensory stimulus application time outputted from the evoked potential measurement procedure control section 20. The evoked potential measurement section 12 amplifies a brain potential inputted thereto by way of an electrode 21, performs, if necessary, pre-processing such as frequency filtering for removal of noise, and outputs a signal 121 regarding a brain potential. The evoked potential recording control section 13 receives a signal 202 regarding an evoked potential measurement starting time and ending time outputted from the evoked potential measurement procedure control section 20 and the signal 121 regarding a brain potential outputted from the evoked potential measurement section 12 and outputs, in response to the signals 202 and 121, a signal 131 regarding a brain potential to the evoked potential recording section 14 after a time at which recording is to be started till another time at which such recording of the brain potential is to be ended. The evoked potential recording section 14 receives the signal 131 regarding a brain potential outputted from the evoked potential recording control section 13 and records and holds the signal 131.

The internal condition estimating physiological measure measurement section 15 amplifies a physiological measure inputted thereto by way of a physiological measure measuring sensor 22, performs, if necessary, preprocessing such as frequency filtering for removal of noise, and outputs a signal 151 regarding a physiological measure. The physiological measure signal recording control section 16 receives a signal 203 regarding a physiological measure starting time and ending time outputted from the evoked potential measurement procedure control section 20 and the signal 151 regarding a physiological measure outputted from the internal condition estimating physiological measure measurement section 15, and outputs, in response to the signals 203 and 151, a signal 161 regarding a physiological measure to the physiological measure signal recording section 17 after a time at which recording of a physiological measure Is to be started till another time at which such recording is to be ended. The physiological measure signal recording section 17 receives the signal 161 regarding a physiological measure outputted from the physiological measure signal recording control section 16 and records and holds the signal 161.

The internal condition estimation section 18 converts the internal condition into a numerical value making use of a signal 171 regarding a physiological measure recorded in the physiological measure signal recording section 17, and outputs a signal 181 of the numerical value regarding the internal condition.

The evoked potential adding and averaging section 19 receives a signal 141 regarding a brain potential recorded in the evoked potential recording section 14, the signal 181 regarding the internal condition outputted from the internal condition estimation section 18, and a signal 204 regarding the number of times of measurement outputted from the evoked potential measurement procedure control section 20. The evoked potential adding and averaging section 19 cumulatively adds, in accordance with the received signals 141, 181 and 204, the brain potential only within brain potential measurement periods within which the value of the internal condition is determined to be higher or lower than a certain value by a number of times equal to the number of times of measurement and calculates an average value among the measurement times.

The evoked potential adoption determination section 24 estimates the quality of each evoked potential data 191 outputted from the evoked potential adding and averaging section 19 and determines whether or not the evoked potential data 191 may be adopted as an evoked potential. If It is determined that the evoked potential data 191 "may be adopted as an evoked potential", the evoked potential adoption determination section 24 sends back evoked potential data 241 to the evoked potential adding and averaging section 19, and extracts a characteristic parameter of the evoked potential data 241 such as a latency or an amplitude. Further, if necessary, the evoked potential adoption determination section 24 performs signal processing such as a frequency analysis.

On the contrary if it is determined by the evoked potential adoption determination section 24 that the evoked potential data 191 "cannot be adopted as an evoked potential", then the evoked potential adoption determination section 24 sends a signal 242 regarding a variation of the measurement procedure to the evoked potential measurement procedure control section 20.

The evoked potential measurement procedure control section 20 outputs, in accordance with the measurement procedure in accordance with which the measurement has been performed by the exprimenter, a signal 201 regarding an application time of a sensory stimulus, a signal 202 regarding an evoked potential measurement starting time and ending time, a signal 203 regarding a physiological measure measurement starting time and ending time, and a signal 204 regarding the number of times of measurement. Further, when the evoked potential measurement procedure control section 20 receives a signal 242 regarding a variation of the measurement procedure from the evoked potential adoption determination section 24, it varies the signal 201 regarding an application time of a sensory stimulus, the signal 202 regarding an evoked potential measurement starting time and ending time, the signal 203 regarding the physiological measure measurement starting time and ending time, or the signal 204 regarding the number of times of measurement.

The sensory stimulus application section 11 may possibly be constituted from a plurality of application sections such as a visual stimulus application section and an auditory sensation application section.

Figure 2:
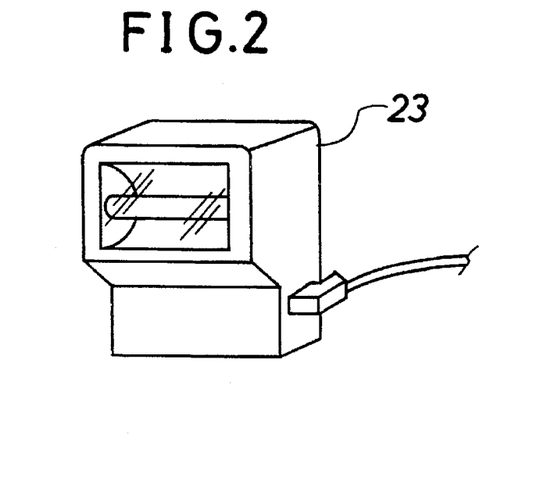
FIG. 2 is a schematic view showing a form of a sensory stimulus application section of the evoked potential measuring apparatus shown in FIG. 1.

Subsequently, an example of measurement of a visually evoked potential when a visual stimulus is applied by a number of times (more than 100 times) greater than an ordinary number of stimulus application times (for example, several tens times) using the evoked potential measuring apparatus of the present embodiment will be described. The sensory stimulus application section 11 may be, for example, such a flash apparatus 23 as shown in FIG. 2. It is otherwise possible to use a CRT display (cathode ray tube) on which a figure or a pattern is displayed or use a light emitting element or the like. The evoked potential measurement procedure control section 20 may be, for example, a personal computer. The exprimenter will input to the evoked potential measurement procedure control section 20 various necessary data including an interval of time (for example, 5+α seconds; α is a random number between 0 and 1) after which the flash apparatus 23 is to be energized to emit light, a period of time (for example, 3 seconds) for which the brain potential is to be measured after the flash apparatus 23 is energized to emit light, another period of time (for example, 3 seconds) for which the internal condition estimating physiological measure is to be measured after the flash apparatus 23 is energized to emit light, the brightness of light to be emitted from the flash apparatus 23, the numbers of times (for example, 100 times) by which the flash apparatus 23 is to be energized to emit light and measurement is to be performed, and the number of times of addition (for example, 50 times) necessary to obtain an evoked potential. Further, the exprimenter will set a measurement procedure. After setting of the measurement procedure is completed, the electrode 21 will be attached to each of a location of the head skin corresponding to the visual cortex in the occipital lobe of the head of the subject and, for example, an earlobe as a 0 volt point. Further, in order to eliminate an influence of external noise, the subject may be covered with an electrostatic shield constructed from, for example, a conductive gauze. As a physiological measure to be utilized for estimation of the internal condition of the subject, for example, a finger plethysmogram known as an autonomic nerve measure is used. Accordingly, a pulsation pickup apparatus (for finger plethysmogram) by NEC San-ei Instruments, Ltd. or a like apparatus may be employed for the physiological measure measuring sensor 22, and a bioelectricity amplification unit 1253A by NEC San-ei Instruments, Ltd. or a like unit may be employed for the internal condition estimating physiological measure measurement section 15. The physiological measure measuring sensor 22 is attached, for example, to the tip of a finger (for example, forefinger). A finger plethysmogram can be obtained as a variation in voltage by those means, and the voltage can be converted into a signal 151 by way of an A/D converter board such as ADX-98E by Canopus Co., Ltd. installed in a personal computer such as PC-9801 by NEC Corporation.

Figure 5:
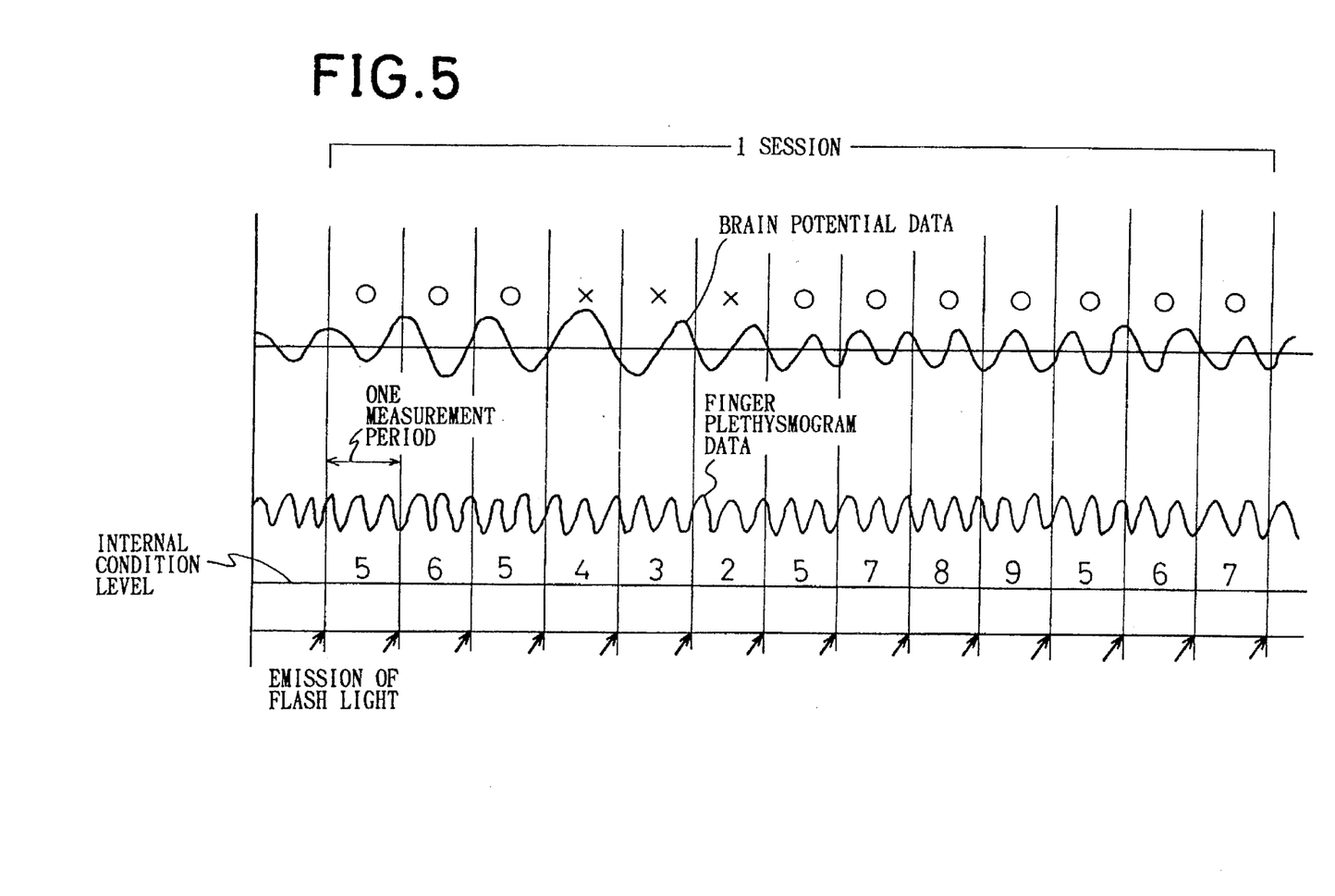
FIG. 5 is a diagram illustrating a relationship among brain potential data, finger plethysmogram data, internal condition level data and emission of flash light during one, session of measurements performed using the evoked potential measuring apparatus of FIG. 1.

After the preparations for measurement of an evoked voltage are completed, the visually evoked voltage is measured based on flash light. The measurement proceeds in accordance with the procedure set in the evoked potential measurement procedure control section 20. Referring also to FIG. 5, each time light is emitted from the flash apparatus 23, a signal of the brain potential for the preset time (for example, 3 seconds) after emission of the flash light is recorded onto the evoked potential recording section 14, which may be, for example, a magnetic disk apparatus or a magnetic tape, by way of the evoked potential recording control section 13. Simultaneously, a signal of the finger plethysmogram for the preset time (for example, for 3 seconds) after emission of the flash light is recorded onto the physiological measure signal recording section 17, which may be, for example, a magnetic disk apparatus or a magnetic tape apparatus, by way of the physiological measure signal recording control section 16. After each lapse of the preset time interval (for example, 5+α seconds), next emission of light is attempted. The procedure described above is repeated by a number of times equal to the preset stimulus application time number (for example, 100 times).

After the measurements by the preset number of times of stimulus application are completed, the internal condition estimation section 18, which may be, for example, a personal computer, converts the measured internal conditions into numerical values based on the finger plethysmogram data recorded on the physiological measure signal recording section 17, and determines whether or not the values of the internal conditions are brain potential data to be added by the evoked potential adding and averaging section 19. The conversion of an internal condition of a human being into a numerical value which makes use of a finger plethysmogram may be performed in accordance with a known method disclosed, for example, in Kenmochi, Kamijo, Iida and Fukuzumi, "A Virtual Reality System Using Psychological and Physiological Data—Estimation of Users' Tension from Plethysmogram and Intelligent Feedback to Virtual Environment—", Proceedings of the 7th Symposium on Biological and Physiological Engineering, November, 1992, pp.277–280. According to the conversion method, amplitude values of the finger plethysmogram measured within one session are divided by a minimum value of the amplitude values selected as a reference value, and values R obtained by such division are determined as estimated values of the internal conditions. From the estimated values R, the internal conditions are classified into such levels as indicated in Table 1 below:

TABLE 1

| Internal Condition Level | |
|---|---|
| 10 | $R \leq 1.5$ |
| 9 | $1.5 < R \leq 2.0$ |
| 8 | $2.0 < R \leq 2.5$ |
| 7 | $2.5 < R \leq 3.0$ |
| 6 | $3.0 < R \leq 3.5$ |
| 5 | $3.5 < R \leq 4.0$ |
| 4 | $4.0 < R \leq 4.5$ |
| 3 | $4.5 < R \leq 5.0$ |
| 2 | $5.0 < R \leq 5.5$ |
| 1 | $5.5 < R$ |

Further, if the internal condition level is, for example, equal to or higher than 5, then the brain potential data obtained in the measurement cycle is determined "to be added", but if the internal condition level is equal to or lower than 4, then the brain potential data obtained in the measurement cycle is determined "not to be added". Thus, for each of the brain potential data obtained by the measurements in the one session, a signal 181 regarding whether the brain potential data should be added or not is outputted.

Figure 3:
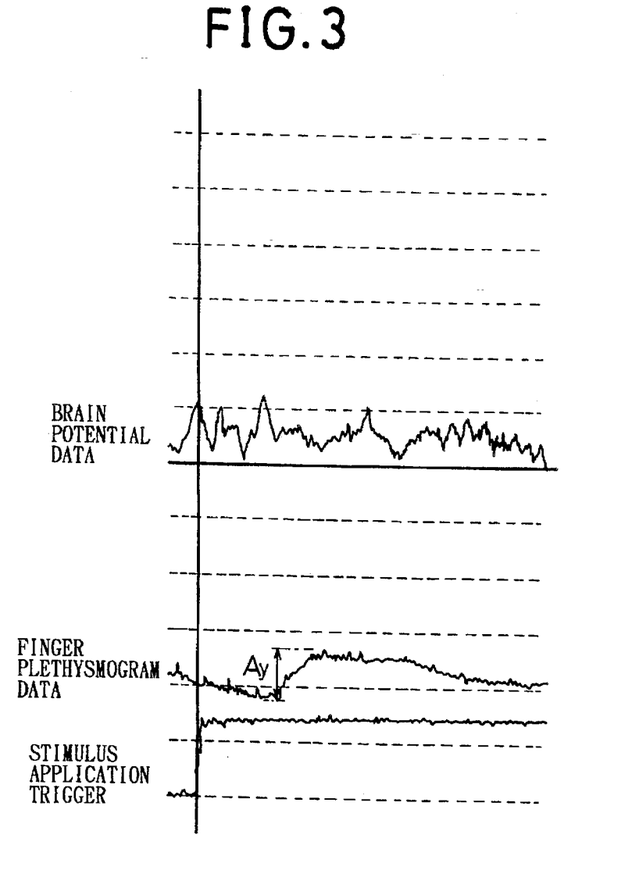
FIG. 3 is a diagram illustrating brain potential data determined "to be added" by an internal condition estimation section of the evoked potential measuring apparatus shown in FIG. 1 and finger plethysmogram data used for the determination.
Figure 4:
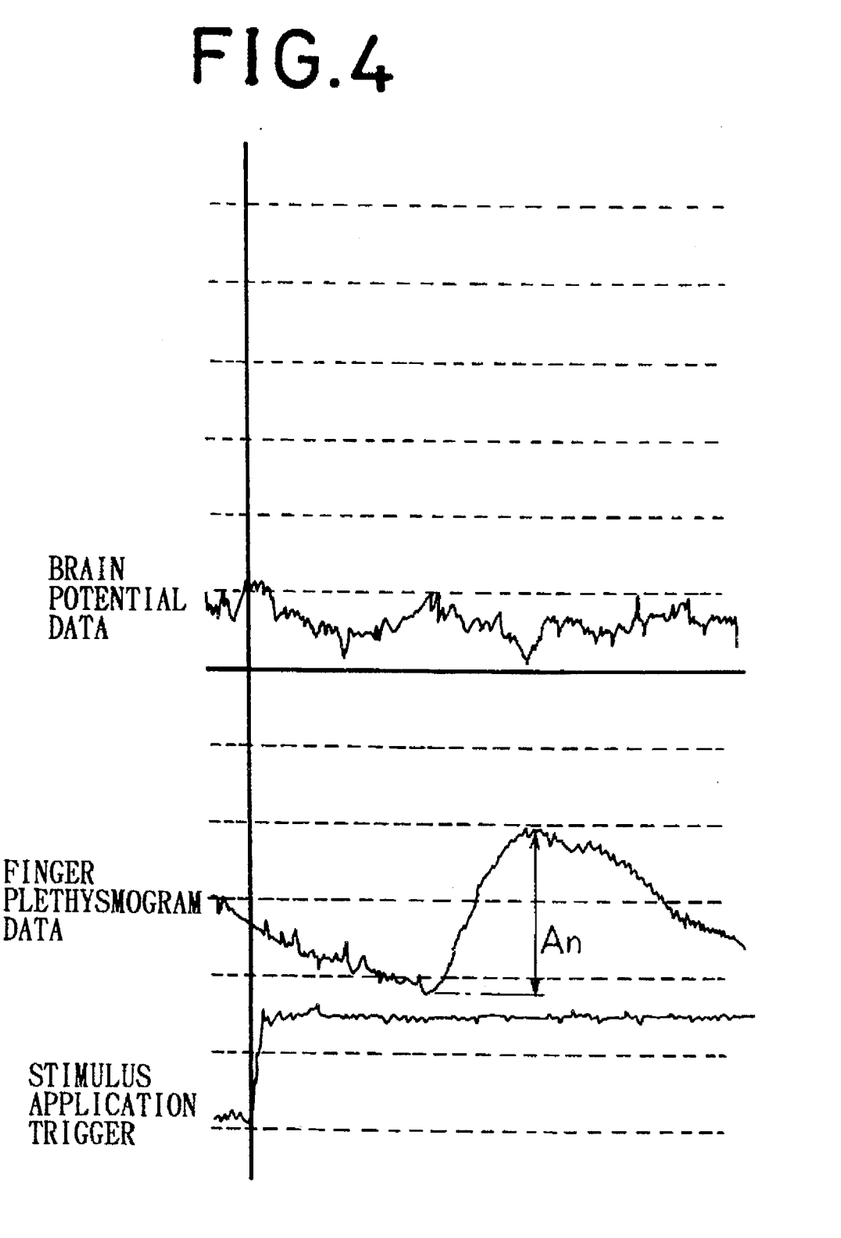
FIG. 4 is a similar view but illustrating brain potential data determined "not to be added" and finger plethysmogram data used for the determination.

A minimum value of amplitude values of a finger plethysmogram during one session and amplitude values at different points of time are determined such that the finger plethysmogram data are retrieved in a window having a width of, for example, 1.5 to 2.0 seconds and a difference in a maximum value and a minimum value of the finger plethysmogram in the window is determined as an amplitude value. FIGS. 3 and 4 illustrate brain potential data (at the upper stage) and finger plethysmogram data (at the medium stage) after digitization by 200 Hz. In FIGS. 3 and 4, the internal condition level values R are calculated from amplitude values Ay and An of the finger plethysmograms detected using a window, respectively. FIGS. 3 and 4 show examples wherein brain potential data are determined "to be added" and determined "not to be added" from the values R of the internal condition level, respectively. It is to be noted that, in each of FIGS. 3 and 4, the rectangular waveform at the lower stage illustrates a condition wherein a sensory stimulus is presented. Further, at the third stage in FIG. 5, examples of the value R of the internal condition level obtained in such a manner as described above are shown.

Subsequently, the evoked potential adding and averaging section 19, which may be, for example, a personal computer, performs, based on the brain potential data 141 detected successively and recorded on the evoked potential recording section 14 and the signal 181 regarding whether or not each of the brain potential data outputted from the internal condition estimation section 18 should be added, cumulative addition of only those of the brain potential data obtained at equal points of time after each emission of light from the flash apparatus which have been determined to be added. In FIG. 5, each mark o shown above the waveform at the first stage, which shows measured brain potential data, represents that the brain potential data to which the mark is applied should be added since the corresponding internal condition level value R in the example shown is equal to or higher than 5 whereas each mark x represents that the corresponding brain potential data should not be added since the corresponding internal condition level value R is equal to or lower than 4. Thus, in this instance, the evoked potential adding and averaging section 19 cumulatively adds only such brain potential data as described above to each of which the mark o is applied. Then, the evoked potential adding and averaging section 19 calculates an average value among the points of time. The average value constitutes evoked potential data.

The evoked potential adoption determination section 24, which may be, for example, a personal computer, receives the evoked potential data 191 outputted from the evoked potential adding and averaging section 19, converts the quality of the evoked potential data 191 into a numerical value, and determines whether or not the evoked potential data 191 may be adopted as an evoked potential. As an index representing the quality of the evoked potential data, for example, a S/N ratio can be used. The S/N ratio is a ratio of a signal (S) to noise (N). Here, the signal corresponds to the evoked potential data 191 obtained from the evoked potential adding and averaging section 19. Meanwhile, for the noise, a ± (plus-minus) average may be used as an estimated value. According to, for example, H. Schimmel, "The ± reference: Accuracy of estimated mean components in average response studies", *Science*, Vol. 157, 1967, pp.92–94, a plus-minus average can be obtained in adding and averaging processing of an evoked potential by adding responses (waveforms) to even-numbered stimulus applications but subtracting responses (waveforms) to odd-numbered stimulus applications. Accordingly, making use of the brain potential signal 141 corresponding to each stimulus application used for the adding and averaging processing of the evoked potential data 191, a plus-minus average can be obtained by adding the brain potential signal 141 corresponding to each even-numbered stimulus application but subtracting the brain potential signal 141 corresponding to each odd-numbered stimulus application. Further, as an estimated value of the S/N ratio, for example, the following expression (1) can be used:

$$\frac{\sum_{t=t_s}^{t_e}(S(t)-N(t))^2}{\sum_{t=t_s}^{t_e}S^2(t)} \times 100(\%), \quad (1)$$

where S(t) is the value of the evoked potential data 191 at the time t, N(t) is the value of the plus-minus average at the time t, and $t_s$ and $t_e$ are the starting time and the ending time of evoked voltage measurement.

For example, if the value of the expression above is equal to or higher than 90%, then it is determined that the value of the evoked potential data 191 may be adopted as an evoked potential, but if the value of the expression is lower than 90%, then it is determined that the value of the evoked potential data 191 cannot be adopted as an evoked potential.

If it is determined by the evoked potential adoption determination section 24 that the value of the evoked potential data 191 "may be adopted", then the evoked potential adoption determination section 24 sends back evoked potential data 241 to the evoked potential adding and averaging section 19, and extracts a characteristic parameter such as a latency or an amplitude of the evoked potential data 241. Further, if necessary, the evoked potential adoption determination section 24 performs signal processing such as frequency analysis.

If it is determined that the value of the evoked potential data 191 "cannot be adopted as an evoked potential", then the evoked potential adoption determination section 24 sends a signal 242 regarding variation of the measurement procedure to the evoked potential measurement procedure control section 20. The evoked potential measurement procedure control section 20 varies, in accordance with the signal 242 regarding variation of the measurement procedure outputted from the evoked potential adoption determination section 24, at least one of the signal 202 regarding the application time of a sensory stimulus, the signal 203 regarding the starting time and the ending time of a physiological measure measurement and the signal 204 regarding the number of measurement times.

After the variation of the measurement procedure has been completed, the evoked potential measurement procedure control section 20 sends a signal 201 regarding the varied application time of a sensory stimulus, a signal 202 regarding the varied starting time or the varied ending time of evoked potential measurement, a signal 203 regarding the varied starting time or the varied ending time of physiological measure measurement, or a signal 204 regarding the varied number of measurement times to the sensory stimulus application section 11, the evoked potential recording control section 13, the physiological measure signal recording control section 16 or the evoked potential adding and averaging section 19, respectively, to start measurement of the evoked potential.

The procedure described above is repeated until evoked potential data obtained by the evoked potential adding and averaging section 19 is adopted as an evoked potential.

Having now fully described the invention, it will be apparent to one of ordinary skill in the art that many changes and modifications can be made thereto without departing from the spirit and scope of the invention as set forth herein.

What is claimed is:

1. An evoked potential measuring apparatus, comprising:

sensory stimulus application means for applying a sensory stimulus to a subject;

evoked potential measurement means for measuring and amplifying a brain potential evoked in response to the sensory stimulus applied to the subject;

evoked potential recording control means for controlling recording of a brain potential signal outputted from said evoked potential measurement means;

evoked potential recording means for recording a brain potential signal outputted from said evoked potential recording control means;

internal condition estimating physiological measure measurement means for measuring a physiological measure to be used for estimation of an internal condition of the subject;

physiological measure signal recording control means for controlling recording of a physiological measure signal outputted from said internal condition estimating physiological measure measurement means;

physiological measure signal recording means for recording a physiological measure signal outputted from said physiological measure signal recording control means;

internal condition estimation means for estimating the internal condition of the subject using a physiological measure signal outputted from said physiological measure signal recording means;

evoked potential adding and averaging means for adding and averaging a brain potential signal outputted from said evoked potential measurement means in accordance with the internal condition of the subject based on a result of estimation of the internal condition of said internal condition estimation means;

evoked potential adoption determination means for estimating a quality of an evoked potential outputted from said evoked potential adding and averaging means to determine whether or not the evoked potential may be adopted; and evoked potential measurement procedure control means for controlling said sensory stimulus application means, said evoked potential recording control means, said physiological measure signal recording control means and said evoked potential adding and averaging means in accordance with a procedure for measurement of an evoked potential and a physiological measure for estimation of an internal condition.

2. An evoked potential measuring apparatus as claimed in claim 1, wherein said evoked potential measurement procedure control means supplies a signal regarding a sensory stimulus application time to said sensory stimulus application means, supplies a signal regarding a starting time and an ending time of evoked potential measurement to said evoked potential recording control means, supplies a signal regarding a starting time and an ending time of physiological measure measurement to said physiological measure signal recording control means, and supplies a signal regarding a number of times of measurement to said evoked potential adding and averaging means.

3. An evoked potential measuring apparatus as claimed in claim 1, wherein said internal condition estimation means converts the internal condition into a numerical value in accordance with the physiological measure signal recorded on said physiological measure signal recording means and determines whether or not the physiological measure signal is a brain potential signal to be added by said evoked potential adding and averaging means.

4. An evoked potential measuring apparatus as claimed in claim 1, wherein said evoked potential adoption determination means employs a signal to noise ratio as an index which indicates a quality of an evoked potential.

5. An evoked potential measuring apparatus as claimed in claim 2, wherein, when said evoked potential adoption determination means determines that the evoked potential cannot be adopted as an evoked potential, said evoked potential adoption determination means sends a signal regarding variation of the measurement procedure to said evoked potential measurement procedure control means, and said evoked potential measurement procedure control means varies, in accordance with the signal regarding variation of the measurement procedure outputted from said evoked potential adoption determination means, at least one of the signal regarding the application time of a sensory stimulus, the signal regarding the starting time and the ending time of evoked potential measurement, the signal regarding the starting time and the ending time of physiological measure measurement, and the signal regarding the number of times of measurement.

6. An evoked potential measuring apparatus as claimed in claim 4, wherein said evoked potential adoption determination means includes means for estimating the quality of the evoked potential by the following equation:

$$\frac{\sum_{t=ts}^{te} (S(t) - N(t))^2}{\sum_{t=ts}^{te} S^2(t)} * 100\%$$

wherein S(t) is a value corresponding to the brain potential signal at a time t, N(t) is a value corresponding to a plus-minus average of the brain potential signal at the time t, ts is the starting time of the evoked potential measurement, and te is the ending time of the evoked potential measurement.

7. An evoked potential measuring apparatus as claimed in claim 6, wherein the means for estimating includes means for calculating the plus-minus average of the brain potential signal N(t) by adding the brain potential signal corresponding to each even-numbered stimulus application and by subtracting each odd-numbered stimulus application, wherein each of said even-numbered and odd-numbered stimulus applications corresponds to a corresponding sensory stimulus applied to the subject by said sensory stimulus application means.

* * * * *